United States Patent
Loveday et al.

(10) Patent No.: US 10,633,406 B1
(45) Date of Patent: Apr. 28, 2020

(54) WATER PROCESSES FOR PRODUCING POLYETHER POLYOLS FROM SOLID POLYHYDROXYL COMPOUNDS

(71) Applicant: COVESTRO LLC, Pittsburgh, PA (US)

(72) Inventors: Anthony R. Loveday, Weirton, WV (US); Daniel R. Wagner, Pittsburgh, PA (US)

(73) Assignee: Covestro LLC, Pittsburgh, PA (US)

( * ) Notice: Subject to any disclaimer, the term of this patent is extended or adjusted under 35 U.S.C. 154(b) by 0 days.

(21) Appl. No.: 16/191,510

(22) Filed: Nov. 15, 2018

(51) Int. Cl.
*C07H 15/08* (2006.01)

(52) U.S. Cl.
CPC .................. *C07H 15/08* (2013.01)

(58) Field of Classification Search
CPC ...................................... C07H 15/08
See application file for complete search history.

(56) References Cited

U.S. PATENT DOCUMENTS

| | | |
|---|---|---|
| 3,085,085 A | 4/1963 | Wismer et al. |
| 3,215,652 A | 11/1965 | Kaplan |
| 3,941,769 A | 3/1976 | Maassen et al. |
| 4,230,824 A | 10/1980 | Nodelman |
| 4,380,502 A | 4/1983 | Müller et al. |
| 5,308,885 A | 5/1994 | Doerge |
| 5,407,596 A | 4/1995 | Mafoti et al. |
| 5,539,006 A | 7/1996 | Doerge et al. |
| 5,625,045 A | 4/1997 | Gupta et al. |
| 5,668,191 A | 9/1997 | Kinkelaar et al. |
| 6,063,309 A | 5/2000 | Hager et al. |
| 6,103,851 A | 8/2000 | Roser et al. |
| 6,218,444 B1 | 4/2001 | Hager et al. |
| 6,380,367 B1 | 4/2002 | Hinz et al. |
| 6,423,759 B1 | 7/2002 | Schilling et al. |
| 6,548,564 B1 | 4/2003 | Adkins et al. |
| 6,599,952 B2 | 7/2003 | Adkins et al. |
| RE38,558 E | 7/2004 | Emanuele et al. |
| 7,127,856 B2 | 10/2006 | Hagen, Jr. et al. |
| 7,168,216 B2 | 1/2007 | Hagen, Jr. |
| 7,574,837 B2 | 8/2009 | Hagen, Jr. et al. |
| 8,716,515 B2 | 5/2014 | Lorenz et al. |
| 8,987,529 B2 | 3/2015 | Lorenz et al. |
| 9,006,499 B2 | 4/2015 | Lorenz et al. |
| 9,067,874 B2 | 6/2015 | Lorenz |
| 10,081,702 B2 | 9/2018 | Loveday et al. |
| 2002/0120026 A1 | 8/2002 | Schilling et al. |
| 2017/0044301 A1* | 2/2017 | Loveday ............ C08G 18/4883 |

* cited by examiner

*Primary Examiner* — Jonathan S Lau
(74) *Attorney, Agent, or Firm* — Donald R. Palladino

(57) ABSTRACT

Batch "water processes" for producing high functionality polyether polyols from polyhydroxyl compounds that are solid at ambient conditions, such as is the case with sucrose, are disclosed. The disclosed processes avoid use of an intermediate dewatering step.

23 Claims, 2 Drawing Sheets

WATER PROCESSES FOR PRODUCING POLYETHER POLYOLS FROM SOLID POLYHYDROXYL COMPOUNDS

FIELD

The present invention relates to batch "water processes" for producing high functionality polyether polyols from polyhydroxyl compounds that are solid at ambient conditions, such as is the case with sucrose, in which an intermediate dewatering step is avoided.

BACKGROUND

Polyether polyols can be produced from polyhydroxyl compounds that are normally solid at ambient conditions, such as sucrose. One commonly used process for producing such polyether polyols is known as the "water process" in which the sucrose is dissolved in water prior to reaction with the selected alkylene oxide(s). The presence of sufficient water to completely dissolve the sucrose has been thought to be necessary since sucrose is non-reactive unless it is in a liquid phase. In addition, due to the presence of sufficient water to dissolve the sucrose, and to get the desired polyol functionality and viscosity, other water soluble liquid organic compounds, such as alcohols and/or amines, such as glycols, i.e., propylene glycol, are also often employed.

The presence of such an amount of water during the reaction of the sucrose with the alkylene oxide, however, can be undesirable. For example, excess water can take up significant space in a batch reactor which might otherwise be used to produce larger batches of polyether polyol. In addition, the presence of water can result in formation of difunctional glycols that reduce the arithmetically calculated functionality of the polyether polyol produced. As a result, in the typical "water process", a dewatering step, usually distillation, is employed after a portion of the alkylene oxide has been added. Such removal of water after adding and reacting a portion of the total alkylene oxide desired reduces the amount of glycols formed and allows for a larger batch size, but still consumes significant time and energy.

A typical "water process" of the prior art is illustrated by FIG. 1. According to this process, a liquid organic compound, such as propylene glycol, is charged to a batch reactor (step 10), along with water (step 15), sucrose (step 20), and an alkali metal hydroxide catalyst (step 25). The water is present in an amount sufficient to dissolve the sucrose at the temperature at which the alkoxylation is to commence. After bringing the reactor to the desired alkoxylation temperature and pressure, a first portion of the alkylene oxide is fed to the reactor (step 30) at a selected feed rate or series of feed rates to conduct a first portion of the alkoxylation reaction. The reactor is then maintained at temperature for a period of time to allow the alkoxylation reaction to continue (step 35). Thereafter, water is removed from the reaction mixture (step 40), typically by distillation, until the water content of the reaction mixture is reduced to less than 10 percent by weight (normally significantly less than 10 weight percent). Then, a second portion of the alkylene oxide is fed to the reactor (step 45) at a selected feed rate or series of feed rates until all desired alkylene oxide has been fed. The reactor temperature may be maintained during this feeding of the second portion of alkylene oxide or it may be increased during the feed, if desired. The reactor is then maintained at temperature or increased in temperature for a period of time (step 50) to allow the alkoxylation reaction to proceed to completion. Thereafter, the resulting polyether polyol proceeds to catalyst neutralization and work-up (step 55).

It would be desirable to provide an improved "water process" for preparing highly functional polyether polyols in a batch process from polyhydroxyl compounds that are solid at ambient conditions, such as sucrose, wherein such a process does not employ a dewatering step prior to completion of the addition of the total alkylene oxide employed. Such a process should be simple and capable of producing a polyol of the same specifications as a similar polyol produced by prior art "water processes". Such a process should also not negatively impact batch size and should not require the use of other materials, such as active hydrogen containing liquid organic compounds, such as glycols, and/or other materials not typically used in a "water process", which may cause greater cost and/or complexity, for example.

The present invention has been made in view of the foregoing desire.

SUMMARY

In certain respects, the specification relates to batch processes for producing a polyether polyol having an arithmetically calculated functionality of 1.9 to 5.8 and an OH number of 360 mg KOH/g polyol to 725 mg KOH/g polyol by an alkoxylation reaction. These batch processes comprise: (a) providing a slurry that: (i) has a temperature of from 80° C. to 150° C., and (ii) consists essentially of: (1) a polyhydroxyl compound which melts above 95° C. or decomposes before melting and has a hydroxyl group functionality greater than or equal to 4, (2) water present in an amount of at least 0.09 grams of water per gram of the polyhydroxyl compound and less than the amount necessary to solubilize all of the polyhydroxyl compound in the slurry at the temperature of the slurry at the commencement of the alkoxylation reaction, and (3) an alkali metal hydroxide, and (b) reacting the slurry of step (a) with an alkylene oxide to form the polyether polyol. These processes also do not include a dewatering step prior to completion of step (b).

In some respects, the specification relates to batch processes for producing a polyether polyol having an arithmetically calculated functionality of 1.9 to 5.8 and an OH number of 360 mg KOH/g polyol to 725 mg KOH/g polyol, in which these batch processes comprise: (a) providing a slurry that: (i) has a temperature of from 80° C. to 150° C., and (ii) consists essentially of: (1) a polyhydroxyl compound which melts above 95° C. or decomposes before melting and has a hydroxyl group functionality greater than or equal to 4, (2) water present in an amount of at least 0.09 and less than 0.20 grams of water per gram of the polyhydroxyl compound, and (3) an alkali metal hydroxide, and (b) reacting the slurry of step (a) with an alkylene oxide to form the polyether polyol. These processes also do not include a dewatering step prior to completion of step (b).

BRIEF DESCRIPTION OF THE DRAWINGS

Various features and characteristics of the inventions described in this specification may be better understood by reference to the accompanying figures, in which.

Figure 1:
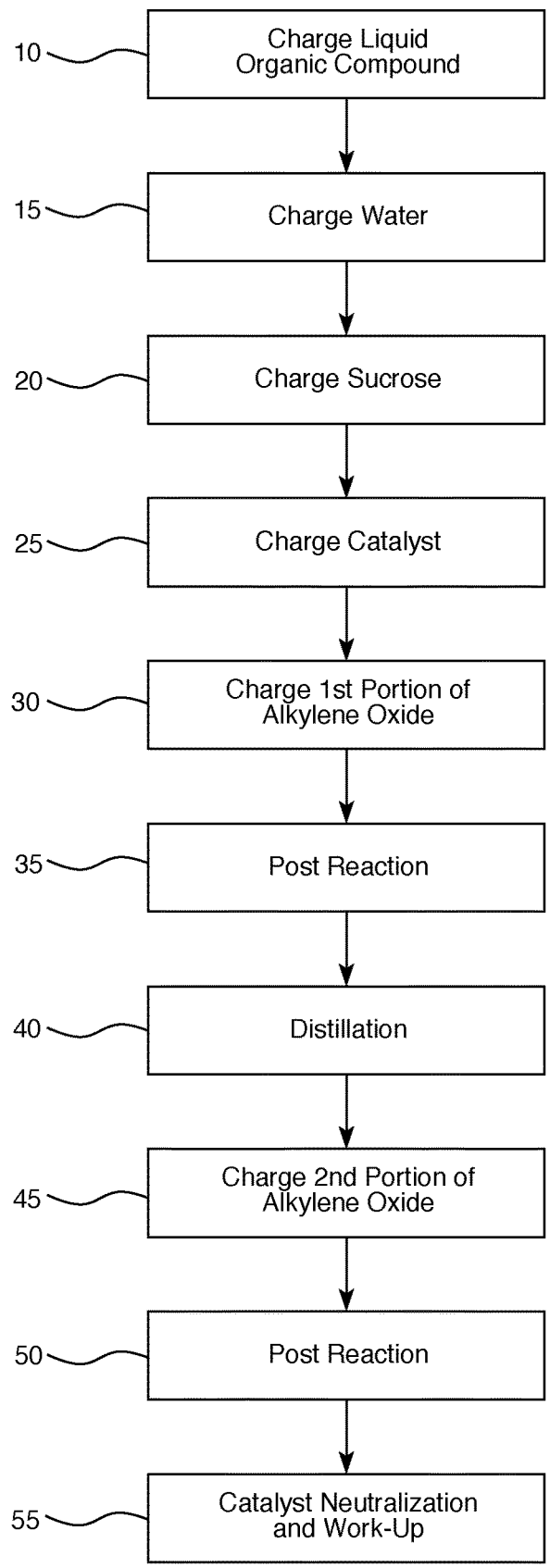
FIG. 1 is a flow chart of a method for producing sucrose based polyols according to the prior art.

The reader will appreciate the foregoing features and characteristics, as well as others, upon considering the following detailed description of the inventions according to this specification.

DETAILED DESCRIPTION

Various embodiments are described and illustrated in this specification to provide an overall understanding of the structure, function, properties, and use of the disclosed inventions. It is understood that the various embodiments described and illustrated in this specification are non-limiting and non-exhaustive. Thus, the invention is not limited by the description of the various non-limiting and non-exhaustive embodiments disclosed in this specification. The features and characteristics described in connection with various embodiments may be combined with the features and characteristics of other embodiments. Such modifications and variations are intended to be included within the scope of this specification. As such, the claims may be amended to recite any features or characteristics expressly or inherently described in, or otherwise expressly or inherently supported by, this specification. Further, Applicant(s) reserve the right to amend the claims to affirmatively disclaim features or characteristics that may be present in the prior art. Therefore, any such amendments comply with the requirements of 35 U.S.C. § 112 and 35 U.S.C. § 132(a). The various embodiments disclosed and described in this specification can comprise, consist of, or consist essentially of the features and characteristics as variously described herein.

Any patent, publication, or other disclosure material identified herein is incorporated by reference into this specification in its entirety unless otherwise indicated, but only to the extent that the incorporated material does not conflict with existing definitions, statements, or other disclosure material expressly set forth in this specification. As such, and to the extent necessary, the express disclosure as set forth in this specification supersedes any conflicting material incorporated by reference herein. Any material, or portion thereof, that is said to be incorporated by reference into this specification, but which conflicts with existing definitions, statements, or other disclosure material set forth herein, is only incorporated to the extent that no conflict arises between that incorporated material and the existing disclosure material. Applicant(s) reserves the right to amend this specification to expressly recite any subject matter, or portion thereof, incorporated by reference herein.

In this specification, other than where otherwise indicated, all numerical parameters are to be understood as being prefaced and modified in all instances by the term "about", in which the numerical parameters possess the inherent variability characteristic of the underlying measurement techniques used to determine the numerical value of the parameter. At the very least, and not as an attempt to limit the application of the doctrine of equivalents to the scope of the claims, each numerical parameter described in the present description should at least be construed in light of the number of reported significant digits and by applying ordinary rounding techniques.

Also, any numerical range recited in this specification is intended to include all sub-ranges of the same numerical precision subsumed within the recited range. For example, a range of "1.0 to 10.0" is intended to include all sub-ranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited in this specification is intended to include all lower numerical limitations subsumed therein and any minimum numerical limitation recited in this specification is intended to include all higher numerical limitations subsumed therein. Accordingly, Applicant(s) reserves the right to amend this specification, including the claims, to expressly recite any sub-range subsumed within the ranges expressly recited herein. All such ranges are intended to be inherently described in this specification such that amending to expressly recite any such sub-ranges would comply with the requirements of 35 U.S.C. § 112 and 35 U.S.C. § 132(a).

The grammatical articles "one", "a", "an", and "the", as used in this specification, are intended to include "at least one" or "one or more", unless otherwise indicated. Thus, the articles are used in this specification to refer to one or more than one (i.e., to "at least one") of the grammatical objects of the article. By way of example, "a component" means one or more components, and thus, possibly, more than one component is contemplated and may be employed or used in an implementation of the described embodiments. Further, the use of a singular noun includes the plural, and the use of a plural noun includes the singular, unless the context of the usage requires otherwise.

As used herein, the term "functionality" refers to the average number of reactive hydroxyl groups, —OH, present per molecule of a polyol or polyol blend that is being described. As used in this specification, the "arithmetically calculated functionality" of a polyol is based on resin solids and is calculated by adding reacted water with the hydroxyl equivalents of the reacted other polyhydroxyl compound(s), such as sucrose, divided by the hydroxyl equivalents of the reacted water multiplied by its functionality (2) plus the hydroxyl equivalents of the reacted other polyhydroxyl compound(s) sucrose multiplied by their functionality, such as (8) in the case of sucrose. The amount of reacted water is calculated by analyzing, using gas chromatography, the weight percent of glycol in the resultant polyol.

As used herein, the term "hydroxyl number" refers to the number of reactive hydroxyl groups available for reaction, and is expressed as the number of milligrams of potassium hydroxide equivalent to the hydroxyl content of one gram of the polyol, and is determined according to ASTM D4274-16. The term "equivalent weight" refers to the weight of a compound divided by its valence. For a polyol, the equivalent weight is the weight of the polyol that will combine with an isocyanate group, and may be calculated by dividing the molecular weight of the polyol by its functionality. The equivalent weight of a polyol may also be calculated by dividing 56,100 by the hydroxyl number of the polyol— Equivalent Weight (g/eq)=(56.1×1000)/OH number.

The viscosity values of a polyol reported herein refer to a viscosity determined using an Anton-Paar SVM 3000 viscometer at 25° C. that has been demonstrated to give equivalent results as can be generated with ASTM-D4878-15, in which the instrument has been calibrated using mineral oil reference standards of known viscosity.

As indicated, certain embodiments of the present specification are directed to batch processes for producing a polyether polyol. As used herein, "batch" refers to a reaction process in which all the reactants are charged into a reactor and are processed there before the product is discharged, and is to be distinguished from "continuous reaction processes" in which reactants are introduced into and product withdrawn simultaneously from a reactor in a continuous manner.

The polyether polyols produced according to the batch processes of the present specification have an arithmetically calculated functionality of 1.9 to 5.8, such as 3.0 to 5.5, or, in some cases 4.6 to 5.3. The polyether polyols produced according to the batch process of the present specification have a hydroxyl number of 360 mg KOH/g polyol to 725 mg KOH/g polyol, such as 400 mg KOH/g polyol to 600 mg KOH/g polyol, or, in some cases, 440 mg KOH/g polyol to 490 mg KOH/g polyol. In some embodiments, the polyether polyols produced according to the batch process of the present specification have a viscosity at 25° C. of 500 mPa·s to 50,000 mPa·s, such as 20,000 mPa·s to 40,000 mPa·s, or, in some cases, 30,000 mPa·s to 38,000 mPa·s. In some embodiments, the polyether polyols produced according to the batch process exhibit a color of no more than 9, no more than 7, or, in some cases, no more than 6 according to the Gardner Color Scale (determined according to ASTM D1544-04 (2018)).

The batch processes of the present specification comprise providing a slurry that: (i) has a temperature of from 80° C. to 150° C., such as 85° C. to 130° C., and (ii) consists essentially of: (1) a polyhydroxyl compound which melts above 95° C. or decomposes before melting and has a hydroxyl group functionality greater than or equal to 4, (2) water present in an amount of at least 0.09 grams water per gram of the polyhydroxyl compound and less than the amount necessary to solubilize all of the polyhydroxyl compound in the slurry at the temperature of the slurry, and (3) an alkali metal hydroxide. As used herein, the term "slurry" means a two-phase suspension of solid particles in a liquid. As used herein, "consisting essentially of" or "consists essentially of" means that the composition may include additional ingredients, but only if the additional ingredients do not materially alter the basic characteristics of the composition or processes of this specification. For example, the slurries described herein may, if desired, include small quantities of ingredients other than those listed as (1), (2) and (3) earlier in this paragraph. As used herein, "small quantities" means that the slurry contains less than 10% by weight, such as less than 5% by weight, less than 2% by weight, or, in some cases, less than 1% by weight, of such other ingredients.

Figure 2:
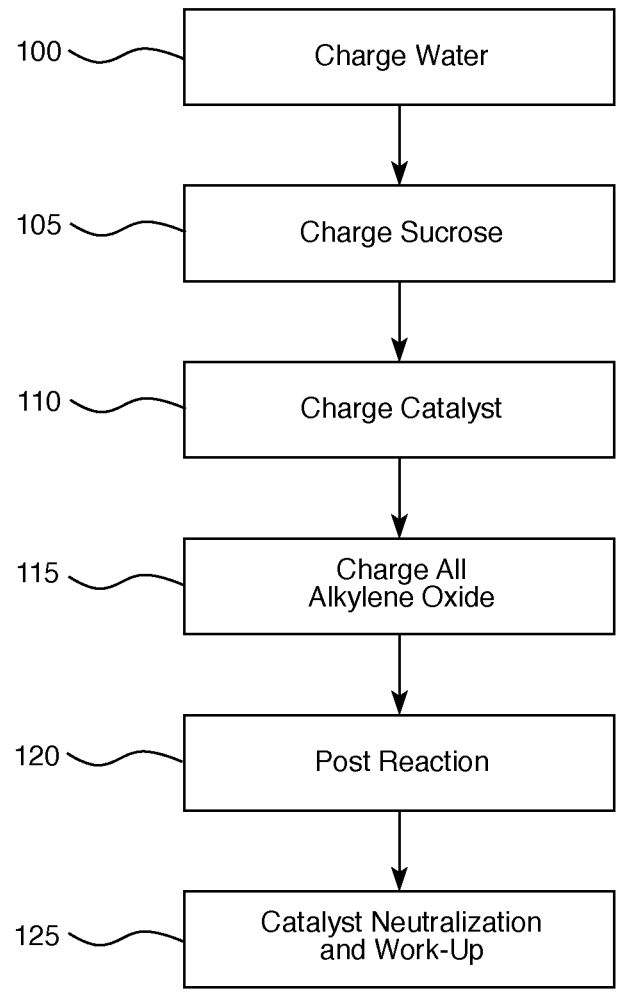
FIG. 2 is a flow chart of a method for producing sucrose based polyols according to an embodiment of the present specification.

An embodiment of a process according to the present specification is illustrated by FIG. 2. According to this embodiment, water (step 100), sucrose (step 105), and an alkali metal hydroxide catalyst (step 110) are charged to a suitable batch alkoxylation reactor. The water is present in an amount sufficient to (i) suspend the sucrose, (ii) to make a slurry that is of sufficiently low viscosity that it is easily stirred in a mechanically agitated vessel, and (iii) attain the desired final functionality of the polyol, but not in an amount sufficient to dissolve all of the sucrose at the temperature at which the alkoxylation is to commence. After bringing the reactor to the desired alkoxylation temperature and pressure, all of the desired alkylene oxide is fed to the reactor (step 115) at a selected feed rate or series of feed rates to conduct the alkoxylation reaction. The reactor temperature may be maintained during this feeding of the alkylene oxide or it may be increased during the feed, if desired. The reactor is then maintained at temperature or increased in temperature for a period of time to allow the alkoxylation reaction to continue until completion (step 120). Thereafter, the resulting polyether polyol proceeds to catalyst neutralization and work-up (step 125).

Thus, in some embodiments, the slurry is prepared by first combining the alkali metal hydroxide with water to form an alkali metal hydroxide/water solution. Suitable alkali metal hydroxides include any of those known to catalyze the alkoxylation reaction, specific examples of which include sodium hydroxide and potassium hydroxide. The alkali metal hydroxide is itself often in the form of an aqueous solution. In some cases, the amount of alkali metal hydroxide used can vary anywhere from 0.01 to 5% by weight, such as 0.1 to 3% by weight, or 1 to 3% by weight, based on the total weight of the slurry. With respect to the alkali metal hydroxide/water solution, the amount of alkali metal hydroxide used is, in some cases, 5 to 60% by weight, based on the total weight of the solution, with the remainder of the solution consisting essentially of water.

According to certain methods for preparing the slurry used in the processes of the present specification, after the alkali metal hydroxide/water solution is formed, the solution is adjusted to an elevated temperature of, for example, at least 50° C., such as 50° C. to 90° C. or 60° C. to 80° C. Then, once the desired temperature is reached, the polyhydroxyl compound which melts above 95° C. or decomposes before melting and has a hydroxyl group functionality greater than or equal to 4, is added to the alkali metal hydroxide/water solution to thereby form the slurry described in this specification. It will be appreciated, however, that the foregoing polyhydoxyl compound could be added to the alkali metal hydroxide/water solution without first elevating the temperature of the solution, if desired.

Solid polyhydroxyl compounds that have a hydroxyl group functionality of at least 4 and melt at a temperature above 95° C. or decompose before melting, which are suitable for use in the processes of this specification, include pentaerythritol, dipentaerythritol, glucose, sorbitol, lactose, mannitol, fructose, sucrose, hydrolyzed starches, saccharide and polysaccharide derivatives such as alpha-methylglucoside and alpha-hydroxyethyl-gluco side.

In certain embodiments, however, such a solid polyhydroxyl compound comprises, or, in some cases, consists essentially of or consists of, sucrose. As used herein, "sucrose" refers to a crystalline disaccharide having D-fructosyl and D-glucosyl moieties, having the structure:

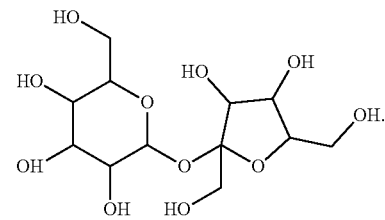 [SMILES: OCC1OC(OC2(CO)OC(CO)C(O)C2O)C(O)C(O)C1O]

In the slurries utilized in the processes described in this specification, however, it is critical that the water is present in an amount of at least 0.09 grams of water per gram of the foregoing polyhydoxyl compound. In some embodiments, water is present in a higher amount, such as at least 0.10, at least 0.12, at least 0.14, or at least 0.16 grams of water per gram of the foregoing polyhydroxyl compound.

It is also critical, with respect to the slurries utilized in the processes described in this specification, that the water is present in an amount less than the amount necessary to solubilize all of the polyhydroxyl compound in the slurry at the temperature of the slurry at the commencement of the alkoxylation reaction. For example, in the case of sucrose and water, it is known that the mass of sucrose that is dissolved by a given mass of water varies with temperature.

In particular, as illustrated in the table below, that mass of sucrose dissolved by 100 grams of water increases with temperature.

| Temperature (° C.) | Grams of sucrose dissolved by 100 grams of water |
|---|---|
| 0 | 179.2 |
| 5 | 184.7 |
| 10 | 190.5 |
| 15 | 197.0 |
| 20 | 203.9 |
| 25 | 211.4 |
| 30 | 219.5 |
| 35 | 228.4 |
| 40 | 238.1 |
| 45 | 248.7 |
| 50 | 260.4 |
| 55 | 273.1 |
| 60 | 287.3 |
| 65 | 302.9 |
| 70 | 320.5 |
| 75 | 339.9 |
| 80 | 362.1 |
| 85 | 386.8 |
| 90 | 415.7 |
| 95 | 448.6 |
| 100 | 487.2 |

Thus, according to the slurries used in the processes described in this specification in which sucrose is the only solid polyhydroxyl compound used, the upper limit of water present in such a slurry, if the temperature of the slurry at the commencement of the alkoxylation reaction is to be 100° C., would be less than the amount that would provide a weight ratio of sucrose to water of 4.872:1, thereby ensuring that all of the sucrose is not dissolved at the commencement of the alkoxylation reaction.

In embodiments of the processes of the present specification, the slurry is brought to a temperature of from 80° C. to 150° C., such as 85° C. to 130° C. or such as 95° C. to 110° C., for commencement of reaction with an alkylene oxide at a pressure of from 4.3 to 58.0 psia, such as 7.2 to 36.2 psia or, in some cases, 10 to 20 psia. As a result, in some of these cases where sucrose is the only solid polyhydroxyl compound used, the relative ratio of sucrose to water, by mass, in the slurry, is at least 3.87:1, such as at least 4.87:1. In some cases, this relative ratio is significantly higher, such as at least 5:1, at least 7:1, or at least 8:1. Moreover, in some embodiments, sucrose is present in the slurry in an amount of at least 70% by weight, at least 80% by weight, or, in some cases, at least 85% by weight, with the remainder of the slurry consisting essentially of water and alkali metal hydroxide. Thus, in certain embodiments, water may be present in an amount sufficient to only dissolve up to 70% of the mass of sucrose present in the slurry. In some cases water is present in an amount sufficient to dissolve 20% to 60% or, in some cases, 40% to 60%, of the mass of sucrose present in the slurry.

As indicated, in the processes of the present specification, the slurry is reacted with an alkylene oxide to form the polyether polyol. Suitable alkylene oxides include, for example, ethylene oxide, propylene oxide and/or 1,2-butylene oxide. In some embodiments, the alkylene oxide consists essentially of, or consists of, propylene oxide, such as where the alkylene oxide comprises at least 98% by weight of propylene oxide. Moreover, in certain embodiments, the alkylene oxide is utilized in an amount such that each molecule of solid polyhydroxy compound, such as sucrose, is reacted, on average, with from 4 to 32 mols of alkylene oxide, such as 10 to 25 mols alkylene oxide, or 10 to 15 mols alkylene oxide. This alkoxylation reaction is carried out until the desired hydroxyl number is attained.

In some embodiments of the processes of this specification, the slurry is reacted with the alkylene oxide using multiple reaction temperatures. For example, the slurry may be reacted with the alkylene oxide at a first reaction temperature within the range 85° C. to 110° C. until about 1 mol of alkylene oxide has been added per mole of the polyhydroxyl compound that is present, then a second reaction temperature within the range of 120° C. to 150° C. (for speed of reaction).

As indicated earlier, the polyols prepared by the processes of the present specification have a hydroxyl number of from 360 mg KOH/g polyol to 725 mg KOH/g polyol, such as 400 mg KOH/g polyol to 600 mg KOH/g polyol, or, in some cases, 440 mg/KOH/g polyol to 490 mg KOH/g polyol and an arithmetically calculated functionality of from 1.9 to 5.8, such as 3.0 to 5.5, or, in some cases, 4.6 to 5.3.

Notably, in accordance with the processes of the present specification, there is no dewatering step prior to the completion of the alkoxylation.

Following the reaction, the alkali metal hydroxide is neutralized with an acid. Neutralization may be accomplished by mixing the acid and reaction mixture at an elevated temperature, for example around 80° C., with stirring. Neutralization need not be exact neutrality and the reaction mixture may be maintained at a basic or acidic pH, such as a pH of from 2 to 9. In certain embodiments, the acid is added at a level of 0.70 to 1.30, such as 1.00 to 1.10 equivalents of acid per equivalent of the alkali metal hydroxide used for the alkoxylation. The neutralized catalyst may be, although is not necessarily, soluble in the polyether polyol so that the catalyst need not be removed from the resulting polyether polyol composition.

The processes for producing polyether polyols described in this specification have several advantages. These include: (a) reduced usage of raw materials, such as water and/or other liquid hydroxyl functional materials, as compared to prior art water processes; (b) reduced energy consumption through elimination of a dewatering step prior to completion of alkoxylation, thus eliminating a second alkylene oxide addition step with accompanying post-reaction period; (c) significant overall process cycle time reduction relative to prior art water process to produce a polyether polyol of the same specifications; and (d) reduced usage of water allows for formation of highly functional polyether polyols by reducing glycol formation.

The polyether polyols produced by the process described in this specification can be used in a variety of applications. In some cases, however, they are useful for producing rigid polyurethane foams. Such foams can be produced by reacting an organic isocyanate with a polyether polyol produced by the processes of this specification, in the presence of a blowing agent and a catalyst at an isocyanate index of from 0.9 to 3.1, such as 1.05 to 1.55.

Suitable organic isocyanates include aromatic, aliphatic, and cycloaliphatic polyisocyanates and combinations thereof. Examples of useful isocyanates are: diisocyanates such as m-phenylene diisocyanate, p-phenylene diisocyanate, 2,4-toluene diisocyanate, 2,6-toluene diisocyanate, 1,6-hexamethylene diisocyanate, 1,4-hexamethylene diisocyanate, 1,4-cyclohexane diisocyanate, hexahydrotoluene diisocyanate and its isomers, 1,5-naphthylene diisocyanate, 1-methyl-phenyl-2,4-phenyl diisocyanate, 4,4'-diphenylmethane diisocyanate, 2,4'-diphenyl-methane diisocyanate, 4,4'-biphenylene diisocyanate, 3,3'-dimethoxy-4,4'-biphenylene diisocyanate and 3,3'-dimethyl-diphenyl-propane-4,4'-diisocyanate; triisocyanates such as 2,4,6-toluene triisocyanate; and polyisocyanates such as 4,4'-dimethyl-diphenyl-methane-2,2',5,5'-tetraisocyanate and the polymethylene polyphenylpolyisocyanates.

Undistilled or a crude polyisocyanate may also be used in making polyurethanes. The crude toluene diisocyanate obtained by phosgenating a mixture of toluene diamines and the crude diphenylmethane diisocyanate obtained by phosgenating crude diphenylmethanediamine are examples of suitable crude polyisocyanates. Suitable undistilled or crude polyisocyanates are disclosed in U.S. Pat. No. 3,215,652.

In some cases, the polyisocyanates are methylene-bridged polyphenyl polyisocyanates and prepolymers of methylene-bridged polyphenyl polyisocyanates having an average functionality of from 1.8 to 3.5 (such as 2.0 to 3.1) isocyanate moieties per molecule and an NCO content of from about 28 to about 34% by weight, due to their ability to cross-link the polyurethane.

Often, the polyisocyanate is used in an amount such that the isocyanate index (i.e., the ratio of equivalents of isocyanate groups to equivalents of isocyanate-reactive groups) is from 0.9 to 3.0, such as from 1.0 to 1.5. In some cases, the polyether polyol prepared by the processes of the present specification are included in the foam-forming mixture in an amount of from 5 to 35% by weight, based on the total foam-forming mixture, such as from 20 to 30% by weight.

Other polyether polyols (i.e., polyether polyols which are not prepared by the processes described in this specification) known to be useful in the production of rigid polyurethane foams may, if desired, be used in combination with the polyether polyols produced as described herein. When used, these optional polyols are sometimes present in an amount which is no greater than 60%, such as from 20% to 50% of the total amount of polyol.

The blowing agent employed may be any one of the known hydrogen-containing chlorofluorocarbons or hydrogen containing fluorocarbons, as well as halogenated olefins. Suitable halogenated olefins include those containing 3 or 4 carbon atoms, at least one carbon-carbon double bond, and have a boiling point of −25° C. to 40° C. at 1 atm pressure. Some examples of such compounds include trans-1,1,1-trifluoro-3-chloropropene (or HCFO 1233zd(E)), cis-1,1,1,4,4,4-hexafluorobutene (or HFO 1336mzz(Z)), and trans-1,1,1,3-tetrafluoropropene (or HFO 1234ze(E)). Specific examples of fluorocarbons include: 1,1-dichloro-2,2,2-trifluoroethane (HCFC-123), 1,1-dichloro-1-fluoroethane (HCFC-141b), 1,1,1,4,4,4-hexafluorobutane (HFC-356), and 1,1,1,2-tetrafluoroethane (HFC-134a). Hydrocarbons which are known to function as blowing agents in rigid foam systems may also be used, examples of which include: n-pentane, cyclopentane, and isopentane. Mixtures of the HCFC, HFC, HFCO and/or HFO with hydrocarbon blowing agents may also be used. The blowing agent is generally included in the foam-forming mixture in an amount of from 5 to 20% by weight, based on the total foam formulation, preferably from 8 to 16% by weight.

Water may be included in the reaction mixtures as well. When used, the water is often present in an amount of from 0.1% to 2%, based on the total foam formulation. Any of the catalysts known to be useful in the production of rigid polyurethane foams may also be employed, such as tertiary amine catalysts. Specific examples of suitable catalysts include: pentamethyldiethylenetriamine, N—N-dimethylcyclohexylamine, N,N',N"-dimethylamino-propylhexahydrotriazine, and tetramethyl ethylenediamine.

Materials which may optionally be included in the foam-forming mixtures also include chain extenders, crosslinking agents, surfactants, pigments, colorants, fillers, antioxidants, flame retardants, and stabilizers.

Various aspects of the subject matter described herein are set out in the following numbered clauses:

Clause 1. A batch process for producing a polyether polyol having an arithmetically calculated functionality of 1.9 to 5.8, such as 3.0 to 5.5, or, in some cases 4.6 to 5.3, an OH number of 360 mg KOH/g polyol to 725 mg KOH/g polyo, such as 400 mg KOH/g polyol to 600 mg KOH/g polyol, or, in some cases, 440 mg KOH/g polyol to 490 mg KOH/g polyol, optionally a viscosity at 25° C. of 500 mPa·s to 50,000 mPa·s, such as 20,000 mPa·s to 40,000 mPa·s, or, in some cases, 30,000 mPa·s to 38,000 mPa·s, and optionally a color of no more than 9, no more than 7, or, in some cases, no more than 6 according to the Gardner Color Scale (determined according to ASTM D1544-04 (2018)), comprising: (a) providing a slurry that: (i) has a temperature of from 80° C. to 150° C., and (ii) consists essentially of: (1) a polyhydroxyl compound which melts above 95° C. or decomposes before melting and has a hydroxyl group functionality greater than or equal to 4, (2) water present in an amount of at least 0.09 grams of water per gram of the polyhydroxyl compound and less than the amount necessary to solubilize all of the polyhydroxyl compound in the slurry at the temperature of the slurry at the commencement of the alkoxylation reaction, and (3) an alkali metal hydroxide, and (b) reacting the slurry of step (a) with an alkylene oxide to form the polyether polyol, wherein the process does not include a dewatering step prior to completion of step (b).

Clause 2. The process of clause 1, wherein the slurry is prepared by: (a) combining the alkali metal hydroxide with water to form an alkali metal hydroxide/water solution; (b) adjusting the solution to a temperature of 50° C. to 90° C.; and (c) adding the polyhydroxyl compound to the alkali metal hydroxide/water solution.

Clause 3. The process of clause 1 or clause 2, wherein water is present in an amount of at least 0.10, at least 0.12, at least 0.14, or at least 0.16 grams of water per gram of the polyhydroxyl compound.

Clause 4. The process of one of clause 1 to clause 3, wherein the polyhydroxyl compound comprises sucrose.

Clause 5. The process of clause 4, wherein the relative ratio of sucrose to water, by mass, in the slurry, is at least 3.87:1, at least 4.87:1, at least 5:1, at least 7:1, or at least 8:1.

Clause 6. The process of clause 4 or clause 5, wherein sucrose is present in the slurry in an amount of at least 70% by weight, at least 80% by weight, or, at least 85% by weight, with the remainder of the slurry consisting essentially of water and alkali metal hydroxide.

Clause 7. The process of one of clause 4 to clause 6, wherein water is present in an amount sufficient to dissolve up to 70%, such as 20% to 60% or 40% to 60%, of the mass of sucrose present in the slurry.

Clause 8. The process of one of clause 4 to clause 7, wherein sucrose is the only solid polyhydroxyl compound that is used.

Clause 9. The process of one of clause 1 to clause 8, wherein the alkylene oxide comprises at least 98% by weight of propylene oxide.

Clause 10. The process of one of clause 1 to clause 9, wherein the alkylene oxide is utilized in an amount such that each molecule of solid polyhydroxy compound is reacted, on average, with 10 to 25 mols of alkylene oxide.

Clause 11. A batch process for producing a polyether polyol having an arithmetically calculated functionality of 1.9 to 5.8, such as 3.0 to 5.5, or, in some cases 4.6 to 5.3, an OH number of 360 mg KOH/g polyol to 725 mg KOH/g polyo, such as 400 mg KOH/g polyol to 600 mg KOH/g polyol, or, in some cases, 440 mg KOH/g polyol to 490 mg KOH/g polyol, optionally a viscosity at 25° C. of 500 mPa·s to 50,000 mPa·s, such as 20,000 mPa·s to 40,000 mPa·s, or, in some cases, 30,000 mPa·s to 38,000 mPa·s, and optionally a color of no more than 9, no more than 7, or, in some cases, no more than 6 according to the Gardner Color Scale (determined according to ASTM D1544-04 (2018)), comprising: (a) providing a slurry that: (i) has a temperature of from 80° C. to 150° C., and (ii) consists essentially of: (1) a polyhydroxyl compound which melts above 95° C. or decomposes before melting and has a hydroxyl group functionality greater than or equal to 4, (2) water present in an amount of at least 0.09 and less than 0.20 grams of water per gram of the polyhydroxyl compound, and (3) an alkali metal hydroxide, and (b) reacting the slurry of step (a) with an alkylene oxide to form the polyether polyol, wherein the process does not include a dewatering step prior to completion of step (b).

Clause 12. The process of clause 11, wherein the slurry is prepared by: (a) combining the alkali metal hydroxide with water to form an alkali metal hydroxide/water solution; (b) adjusting the solution to a temperature of 50° C. to 90° C.; and (c) adding the polyhydroxyl compound to the alkali metal hydroxide/water solution.

Clause 13. The process of clause 11 or clause 12, wherein water is present in an amount of at least 0.10, at least 0.12, at least 0.14, or at least 0.16 grams of water per gram of the polyhydroxyl compound.

Clause 14. The process of one of clause 11 to clause 13, wherein the polyhydroxyl compound comprises sucrose.

Clause 15. The process of clause 14, wherein the relative ratio of sucrose to water, by mass, in the slurry, is at least 3.87:1, at least 4.87:1, at least 5:1, at least 7:1, or at least 8:1.

Clause 16. The process of clause 14 or clause 15, wherein sucrose is present in the slurry in an amount of at least 70% by weight, at least 80% by weight, or, at least 85% by weight, with the remainder of the slurry consisting essentially of water and alkali metal hydroxide.

Clause 17. The process of one of clause 14 to clause 16, wherein water is present in an amount sufficient to dissolve up to 70%, such as 20% to 60% or 40% to 60%, of the mass of sucrose present in the slurry.

Clause 18. The process of one of clause 14 to clause 17, wherein sucrose is the only solid polyhydroxyl compound that is used.

Clause 19. The process of one of clause 11 to clause 18, wherein the alkylene oxide comprises at least 98% by weight of propylene oxide.

Clause 20. The process of one of clause 11 to clause 19, wherein the alkylene oxide is utilized in an amount such that each molecule of solid polyhydroxy compound is reacted, on average, with 10 to 25 mols of alkylene oxide.

EXAMPLES

Polyether Polyol Example 1

A polyether polyol composition was prepared using the ingredients and amounts listed in Table 1. To prepare the polyether polyol composition, a 20 kg reactor was charged with water, KOH and sugar at ambient temperature with agitation. The total water to sugar ratio was 0.127 g of water per gram of sugar. Oxygen was removed from the reactor by pressurizing the reactor to −25 psig with nitrogen and venting. This was carried out three times and the reactor sealed. The reactor temperature was raised to 100° C. The desired amount of PO was dosed to the reactor at a rate sufficient to maintain the reaction pressure below 40 psig. Once 35% of the desired amount of PO had been fed, the temperature of the reactor was slowly raised to 130° C. Once the desired amount of PO was fed, the reactor was held at 130° C. for a sufficient time to fully react any unreacted PO. After completion of the PO addition, the reactor was cooled to 80° C. and the desired amount of water and sulfuric acid was added to fully neutralize the KOH. The sulfuric acid reacted with the KOH to form insoluble potassium sulfate salts. No visually observable unreacted sugar was present in the crude unrefined polyol composition. The reactor temperature was raised to 115° C. and the mixture was de-watered using vacuum distillation with a slight nitrogen sparge through the mixture. The reactor was cooled to 90° C. and the reactor was charged with BHT and agitated for 30 minutes. The potassium sulfate salts were then filtered from the final polyether polyol. The process time, OH#, viscosity, color, and calculated functionality of the polyol are all set forth in Table 1.

TABLE 1

| | |
|---|---|
| De-ionized water (grams) | 614.4 |
| KOH[2] (grams) | 120.1 |
| Sugar[3] (grams) | 5341.3 |
| PO[1](grams) | 12460.1 |
| Time (hours) | 9.4 |
| De-ionized Water (grams) | 2300.4 |
| Sulfuric Acid[4] (grams) | 49.9 |
| BHT[5] (grams) | 8.6 |
| OH# (mg KOH/g polyol) | 471.3 |
| Viscosity (mPa · s) | 36250 |
| Gardner Color | 4 |
| Calculated Functionality | 5.23 |

[1]Propylene oxide from Lyondell Chemical Company
[2]Aqueous potassium hydroxide (45% solution) from Fisher Scientific
[3]Sugar, granulated from Sam's Club
[4]Sulfuric acid, 96%, from Sigma-Aldrich
[5]Butylated hydroxytoluene from Sigma-Aldrich
[6]Propylene glycol from Univar Polyether Polyol Example 2

A polyether polyol composition was prepared using the ingredients and amounts listed in Table 2. The preparation of the polyol was identical to Example 1 with the following changes: (1) The desired amount of PO was dosed to the reactor at a rate sufficient to maintain the reaction pressure below 35 psig; and (2) Once 40% of the desired amount of PO had been fed, the temperature of the reactor was slowly raised to 130° C. The polyol composition displayed no visible unreacted sugar in the crude unrefined polyol. The process time, OH#, viscosity, color, and calculated functionality of the polyol are all set forth in Table 2.

TABLE 2

| | |
|---|---|
| De-ionized water (grams) | 614.8 |
| KOH[2] (grams) | 120.2 |
| Sugar[3] (grams) | 5343.1 |
| PO[1](grams) | 12465.9 |
| Time (hours) | 13.4 |
| De-ionized Water (grams) | 1148.5 |
| Sulfuric Acid[4] (grams) | 50.0 |
| BHT[5] (grams) | 8.6 |
| OH# (mg KOH/g polyol) | 472.6 |
| Viscosity (mPa · s) | 35167 |

| | |
|---|---|
| Gardner Color | 5 |
| Calculated Functionality | 5.21 |

Polyether Polyol Example 3

A polyether polyol composition was prepared using the ingredients and amounts listed in Table 3. The preparation of the polyol was identical to Example 1 with the following changes: (1) The total water to sugar ratio was 0.095 g of water per gram of sugar; (2) The desired amount of PO was dosed to the reactor at a rate sufficient to maintain the reaction pressure below 39 psig; and (3) Once 35% of the desired amount of PO had been fed, the temperature of the reactor was slowly raised to 130° C. The polyol composition displayed no visible unreacted sugar in the crude unrefined polyol. The process time, OH#, viscosity, color, and calculated functionality of the polyol are all set forth in Table 3.

TABLE 3

| | |
|---|---|
| De-ionized water (grams) | 432.0 |
| KOH[2] (grams) | 117.1 |
| Sugar[3] (grams) | 5220.0 |
| PO[1] (grams) | 12242.6 |
| Time (hours) | 11.8 |
| De-ionized Water (grams) | 2395.8 |
| Sulfuric Acid[4] (grams) | 46.4 |
| BHT[5] (grams) | 5.7 |
| OH# (mg KOH/g polyol) | 463.9 |
| Viscosity (mPa · s) | 34550 |
| Gardner Color | 7 |
| Calculated Functionality | 5.35 |

Polyether Polyol Example 4

A polyether polyol composition was prepared using the ingredients and amounts listed in Table 4. The preparation of the polyol was identical to Example 1 with the following changes: (1) The total water to sugar ratio was 0.168 g of water per gram of sugar; (2) The reactor temperature was raised to 110° C.; (3) The desired amount of PO was dosed to the reactor at a rate sufficient to maintain the reaction pressure below 52 psig; and (4) Once 68% of the desired amount of PO had been fed, the temperature of the reactor was slowly raised to 130° C. The polyol composition displayed no visible unreacted sugar in the crude unrefined polyol. The process time, OH#, viscosity, color, and calculated functionality of the polyol are all set forth in Table 4.

TABLE 4

| | |
|---|---|
| De-ionized water (grams) | 805.1 |
| KOH[2] (grams) | 122.0 |
| Sugar[3] (grams) | 5200.8 |
| PO[1] (grams) | 11975.9 |
| Time (hours) | 8.8 |
| De-ionized Water (grams) | 2244.9 |
| Sulfuric Acid[4] (grams) | 52.3 |
| BHT[5] (grams) | 5.6 |
| OH# (mg KOH/g polyol) | 506.2 |
| Viscosity (mPa · s) | 26600 |
| Gardner Color | 9 |
| Calculated Functionality | 4.73 |

Polyether Polyol Example 5

A polyether polyol composition was prepared using the ingredients and amounts listed in Table 5. The preparation of the polyol was identical to Example 1 with the following changes: (1) The total water to sugar ratio was 0.098 g of water per gram of sugar; (2) The reactor temperature was raised to 110° C.; (3) The desired amount of PO was dosed to the reactor at a rate sufficient to maintain the reaction pressure below 55 psig; and (4) Once 43% of the desired amount of PO had been fed, the temperature of the reactor was slowly raised to 130° C. The polyol composition displayed no visible unreacted sugar in the crude unrefined polyol. The process time, OH#, viscosity, color, and calculated functionality of the polyol are all set forth in Table 5.

TABLE 5

| | |
|---|---|
| De-ionized water (grams) | 466.6 |
| KOH[2] (grams) | 127.2 |
| Sugar[3] (grams) | 5462.7 |
| PO[1] (grams) | 12445.3 |
| Time (hours) | 17.2 |
| De-ionized Water (grams) | 2283.4 |
| Sulfuric Acid[4] (grams) | 53.4 |
| BHT[5] (grams) | 5.7 |
| OH# (mg KOH/g polyol) | 489.8 |
| Viscosity (mPa · s) | 32750 |
| Gardner Color | 11 |
| Calculated Functionality | 5.04 |

Polyether Polyol Example 6 (Comparative)

A polyether polyol composition was prepared using the ingredients and amounts listed in Table 6. The preparation of the polyol was identical to Example 1 with the following changes: (1) The total water to sugar ratio was 0.080 g of water per gram of sugar; (2) The desired amount of PO was dosed to the reactor at a rate sufficient to maintain the reaction pressure below 50 psig. The polyol displayed unreacted sugar settling in sample jars of the "crude", unrefined polyol. A representative sample of the crude polyol was dissolved in an equal volume of acetone and the unreacted sugar was filtered. The unreacted sugar was allowed to dry and weighed. The unreacted sugar was found to be 0.26 wt. % of the polyol which translates to 0.89 wt. % (47.7 grams) of the sugar charged did not alkoxylate. The process time, OH#, viscosity, color, and calculated functionality of the polyol are all set forth in Table 6.

TABLE 6

| | |
|---|---|
| De-ionized water (grams) | 362.0 |
| KOH[2] (grams) | 120.0 |
| Sugar[3] (grams) | 5341.0 |
| PO[1] (grams) | 12463.1 |
| Time (hours) | 9.7 |
| De-ionized Water (grams) | 2267.0 |
| Sulfuric Acid[4] (grams) | 50.0 |
| BHT[5] (grams) | 8.5 |
| OH# (mg KOH/g polyol) | 446.0 |
| Viscosity (mPa · s) | 32900 |
| Gardner Color | 2 |
| Calculated Functionality | 5.66 |

Polyether Polyol Example 7 (Prior Art "Water Process"—Comparative)

A polyether polyol composition was prepared using the ingredients and amounts listed in Table 7. To prepare the polyether polyol composition, the 20 kg reactor was charged with propylene glycol (PG), water, KOH and sugar at ambient temperature with agitation. The total water to sugar ratio was 0.214 g of water per gram of sugar. Oxygen was removed from the reactor by pressurizing the reactor to ~25 psig with nitrogen and venting. This was carried out three times and the reactor sealed. The reactor temperature was raised to 100° C. The desired amount of PO1 was dosed to the reactor at a rate sufficient to maintain the reaction pressure below 52 psig. Once the desired amount of PO1 was fed, the reactor was held at 100° C. for a sufficient time to fully react any unreacted PO. The temperature of the reactor was then lowered to 95° C. and vacuum distillation was conducted for ~46 minutes. The distillation was stopped and a sample taken for water analysis. The water result was deemed too high (1.73%) and the distillation was resumed. The distillation was stopped (total vacuum distillation was ~58 minutes) and a second sample taken for water analysis. This result was acceptable (0.87%) and the reactor was heated to 115° C. The desired amount of PO2 was dosed to the reactor at a rate sufficient to maintain the reaction pressure below 32 psig. Once the desired amount of PO2 was fed, the reactor was held at 115° C. for a sufficient time to fully react any unreacted PO. After completion of the PO2 addition, the reactor was cooled to 80° C. and the desired amount of water and sulfuric acid was added to fully neutralize the KOH. The sulfuric acid reacted with the KOH to form insoluble potassium sulfate salts. The reactor temperature was raised to 115° C. and the mixture was de-watered using vacuum distillation with a slight nitrogen sparge through the mixture. The reactor was cooled to 90° C. and the reactor was charged with BHT and agitated for 30 minutes. The potassium sulfate salts were then filtered from the final polyether polyol. The process time, OH#, viscosity, color, and calculated functionality of the polyol are all set forth in Table 7.

TABLE 7

| | |
|---|---|
| De-ionized water (grams) | 1077.5 |
| KOH$^2$ (grams) | 126.1 |
| Sugar$^3$ (grams) | 5347.5 |
| PG$^6$ (grams) | 432.2 |
| PO1$^1$ (grams) | 5989.2 |
| PO1 Reaction (hours) | 12.9 |
| PO1 Distill (hours) | 1.8 |
| PO2 (grams) | 6218.4 |
| PO2 Reaction (hrs) | 5.9 |
| Total Time (hrs) | 20.6 |
| De-ionized Water (grams) | 2253.6 |
| Sulfuric Acid$^4$ (grams) | 52.2 |
| BHT$^5$ (grams) | 8.4 |
| OH# | 468.6 |
| Viscosity (mPa · s) | 34800 |
| Gardner Color | 7 |
| Calculated Functionality | 5.23 |

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:
1. A batch process for producing a polyether polyol having an arithmetically calculated functionality of 1.9 to 5.8 and an OH number of 360 mg KOH/g polyol to 725 mg KOH/g polyol by an alkoxylation reaction, comprising:
   (a) providing a slurry that:
      (i) has a temperature of from 80° C. to 150° C., and
      (ii) consists essentially of:
         (1) a polyhydroxyl compound which melts above 95° C. or decomposes before melting and has a hydroxyl group functionality greater than or equal to 4,
         (2) water present in an amount of at least 0.09 grams of water per gram of the polyhydroxyl compound and less than the amount necessary to solubilize all of the polyhydroxyl compound in the slurry at the temperature of the slurry at the commencement of the alkoxylation reaction, and
         (3) an alkali metal hydroxide, and
   (b) reacting the slurry of step (a) with an alkylene oxide to form the polyether polyol,
   wherein the process does not include a dewatering step prior to completion of step (b).
2. The process of claim 1, wherein the slurry is prepared by:
   (a) combining the alkali metal hydroxide with water to form an alkali metal hydroxide/water solution;
   (b) adjusting the solution to a temperature of 50° C. to 90° C.; and
   (c) adding the polyhydroxyl compound to the alkali metal hydroxide/water solution.
3. The process of claim 1, wherein water is present in an amount of at least 0.12 grams of water per gram of the polyhydroxyl compound.
4. The process of claim 1, wherein the polyhydroxyl compound comprises sucrose.
5. The process of claim 4, wherein the relative ratio of sucrose to water, by mass, in the slurry, is at least 3.87:1.
6. The process of claim 5, wherein the relative ratio of sucrose to water, by mass, in the slurry, is at least 5:1.
7. The process of claim 4, wherein sucrose is present in the slurry in an amount of at least 70% by weight, based on the total weight of the slurry.
8. The process of claim 4, wherein water is present in an amount sufficient to dissolve up to 70% of the mass of sucrose present in the slurry.
9. The process of claim 8, wherein water is present in an amount sufficient to dissolve 20% to 60% of the mass of sucrose present in the slurry.
10. The process of claim 4, wherein sucrose is the only solid polyhydroxyl compound that is used.
11. The process of claim 1, wherein the alkylene oxide comprises at least 98% by weight of propylene oxide.
12. The process of claim 1, wherein the alkylene oxide is utilized in an amount such that each molecule of solid polyhydroxy compound is reacted, on average, with 10 to 25 mols of alkylene oxide.
13. A batch process for producing a polyether polyol having an arithmetically calculated functionality of 1.9 to 5.8 and an OH number of 360 mg KOH/g polyol to 725 mg KOH/g polyol, comprising:
   (a) providing a slurry that:
      (i) has a temperature of from 80° C. to 150° C., and
      (ii) consists essentially of:
         (1) a polyhydroxyl compound which melts above 95° C. or decomposes before melting and has a hydroxyl group functionality greater than or equal to 4,
         (2) water present in an amount of at least 0.09 and less than 0.20 grams of water per gram of the polyhydroxyl compound, and
         (3) an alkali metal hydroxide, and
   (b) reacting the slurry of step (a) with an alkylene oxide to form the polyether polyol, wherein the process does not include a dewatering step prior to completion of step (b).

14. The process of claim 13, wherein water is present in an amount of at least 0.12 grams of water per gram of the polyhydroxyl compound.

15. The process of claim 13, wherein the polyhydroxyl compound comprises sucrose.

16. The process of claim 14, wherein the relative ratio of sucrose to water, by mass, in the slurry, is at least 3.87:1.

17. The process of claim 16, wherein the relative ratio of sucrose to water, by mass, in the slurry, is at least 5:1.

18. The process of claim 15, wherein sucrose is present in the slurry in an amount of at least 70% by weight, based on the total weight of the slurry.

19. The process of claim 15, wherein water is present in an amount sufficient to dissolve up to 70% of the mass of sucrose present in the slurry.

20. The process of claim 19, wherein water is present in an amount sufficient to dissolve 20% to 60% of the mass of sucrose present in the slurry.

21. The process of claim 15, wherein sucrose is the only solid polyhydroxyl compound that is used.

22. The process of claim 13, wherein the alkylene oxide comprises at least 98% by weight of propylene oxide.

23. The process of claim 13, wherein the alkylene oxide is utilized in an amount such that each molecule of solid polyhydroxy compound is reacted, on average, with 10 to 25 mols of alkylene oxide.

* * * * *